US012711618B2

(12) United States Patent
Chen et al.

(10) Patent No.: US 12,711,618 B2
(45) Date of Patent: Aug. 18, 2026

(54) DEVICES AND METHODS FOR DETECTING PULMONARY FUNCTION BASED ON LOW-DOSE CT IMAGES

(71) Applicant: TAIPEI MEDICAL UNIVERSITY, Taipei City (TW)

(72) Inventors: David Carroll Chen, Taipei City (TW); Cheng-Yu Chen, Taipei City (TW)

(73) Assignee: TAIPEI MEDICAL UNIVERSITY, Taipei City (TW)

( * ) Notice: Subject to any disclaimer, the term of this patent is extended or adjusted under 35 U.S.C. 154(b) by 440 days.

(21) Appl. No.: 18/335,969

(22) Filed: Jun. 15, 2023

(65) Prior Publication Data

US 2024/0420319 A1 Dec. 19, 2024

(51) Int. Cl.
*G06T 7/00* (2017.01)
*G06V 10/46* (2022.01)
(Continued)

(52) U.S. Cl.
CPC .......... *G06T 7/0012* (2013.01); *G06V 10/462* (2022.01); *G16H 30/40* (2018.01); (Continued)

(58) Field of Classification Search
CPC .................................................... G06T 7/0012
See application file for complete search history.

(56) References Cited

U.S. PATENT DOCUMENTS 8,465,437 B2 6/2013 Avila
8,811,724 B2 * 8/2014 Nielsen ................ G06T 7/0012 382/128
(Continued)

FOREIGN PATENT DOCUMENTS

CN 107397554 A 11/2017
CN 112052896 A 12/2020
(Continued)

OTHER PUBLICATIONS

Chen et al., "MR Image-Based Synthetic CT for IMRT Prostate Treatment Planning and CBCT Image-Guided Localization", Journal of applied clinical medical physics, 2016, vol. 17, No. 3, pp. 236-245.
(Continued)

*Primary Examiner* — Benjamin O Dulaney
(74) *Attorney, Agent, or Firm* — IDEA Intellectual Limited; Sam T. Yip

(57) ABSTRACT

Disclosed are devices and methods for detecting pulmonary function based on low-dose computed tomography (CT) images. The present disclosure provides a method of determining a pulmonary function based on low-dose CT chest images. The method includes receiving a plurality of chest images, the plurality of chest image generated by a low-dose CT method; determining a plurality of regions of interest (ROIs) within each chest image through an image processing model, the plurality of ROIs corresponding to five lung lobes; determining $T_{ij}$ descriptors for the j-th ROI of the i-th chest image, each descriptor associated with the radiodensity value of one or more pixels; and determining whether a pulmonary function of the respective lung lobe is normal or abnormal based on the descriptors.

18 Claims, 5 Drawing Sheets

(51) Int. Cl.
*G16H 30/40* (2018.01)
*G16H 50/20* (2018.01)

(52) U.S. Cl.
CPC ... *G16H 50/20* (2018.01); *G06T 2207/10081* (2013.01); *G06T 2207/20084* (2013.01); *G06T 2207/30061* (2013.01)

(56) References Cited

U.S. PATENT DOCUMENTS

| | | | |
|---|---|---|---|
| 9,504,529 B2 | 11/2016 | Raffy et al. | |
| 10,226,299 B2 | 3/2019 | Raffy et al. | |
| 10,997,475 B2 | 5/2021 | Xu et al. | |
| 11,304,756 B2 | 4/2022 | Raffy et al. | |
| 11,640,661 B2 | 5/2023 | Washko, Jr. et al. | |
| 11,684,293 B2 * | 6/2023 | Slepian | A61B 5/113 600/301 |
| 12,100,493 B2 * | 9/2024 | Culala | A61B 6/50 |
| 2017/0337343 A1 * | 11/2017 | Kakadiaris | G16Z 99/00 |
| 2018/0064830 A1 | 3/2018 | Uber, III | |
| 2019/0027252 A1 | 1/2019 | Calhoun et al. | |
| 2020/0222120 A1 | 7/2020 | Culala | |
| 2020/0238107 A1 * | 7/2020 | Shabtay | A61N 5/0613 |
| 2020/0410670 A1 | 12/2020 | Gerard et al. | |
| 2021/0042564 A1 * | 2/2021 | Xiao | G06T 7/0012 |
| 2021/0059765 A1 * | 3/2021 | Ye | A61B 5/066 |
| 2021/0166391 A1 * | 6/2021 | Hermosillo Valadez | G06N 3/08 |
| 2022/0172353 A1 | 6/2022 | Yi et al. | |
| 2022/0180514 A1 * | 6/2022 | Vlasimsky | A61B 6/5217 |
| 2024/0386552 A1 * | 11/2024 | Peterson | G06T 7/62 |
| 2025/0111516 A1 * | 4/2025 | Slomka | G06T 7/11 |

FOREIGN PATENT DOCUMENTS

| | | |
|---|---|---|
| CN | 112885453 A | 6/2021 |
| CN | 109461495 B | 4/2023 |
| TW | 202141521 A | 11/2021 |
| TW | 202223914 A | 6/2022 |
| WO | 9836683 A1 | 8/1998 |
| WO | 2009102930 A2 | 8/2009 |
| WO | 2015127355 A1 | 8/2015 |

OTHER PUBLICATIONS

Uchiyama et al., "Risk of Radiation Pneumonitis in Patients with Emphysema after Stereotactic Body Radiotherapy for Non-Small Cell Lung Cancer Assessed by Quantitative CT", Molecular and Clinical Oncology, 2020, vol. 13, No. 3.

Lu et al., "Three-Dimensional Lung Medical Image Registration Based on Improved Demons Algorithm", Optik, Elsevier, 2016, vol. 127, No. 4, pp. 1893-1899.

Mets et al., "Identification of Chronic Obstructive Pulmonary Disease in Lung Cancer Screening Computed Tomographic Scans", Jama Network, 2011, vol. 306, No. 16, pp. 1775-1781.

International Search Report and Written Opinion of corresponding PCT Patent Application No. PCT/US2023/074814 mailed on Jan. 22, 2024.

Office Action of corresponding Taiwan patent application No. 112122343 mailed on Jul. 12, 2024.

* cited by examiner

DEVICES AND METHODS FOR DETECTING PULMONARY FUNCTION BASED ON LOW-DOSE CT IMAGES

FIELD OF THE INVENTION

The present disclosure relates to a method for detecting pulmonary function and to related devices. In particular, the present disclosure relates to methods for detecting pulmonary function based on low-dose computed tomography (CT) images, and to related devices.

BACKGROUND

Medical advances and air quality have become critical issues with regard to maintaining health, especially for the lungs. Generally, regular health examinations are useful for detecting possible lungs problems at the earliest possible stage. However, high-radiation examinations may carry undesirable side effects.

Low-radiation examinations may be considered since people consider that radiation may cause health risks. However, it is difficult to determine the extracted data from low-radiation examinations. In addition, low-radiation examinations may result in determination, prediction, or detection of low accuracy due to the low resolution and high noises of low-radiation images. Therefore, improving the accuracy of the determination, prediction, or detection from the low-radiation examinations is essential.

SUMMARY OF THE INVENTION

The present disclosure provides a method of determining a pulmonary function based on low-dose CT chest images. The method includes receiving a plurality of chest images, the plurality of chest images generated by a low-dose CT method; determining a plurality of regions of interest (ROIs) within each chest image through an image processing model, the plurality of ROIs corresponding to five lung lobes; determining $T_{ij}$ descriptors for the j-th ROI of the i-th chest image, each descriptor associated with the radiodensity value of one or more pixels; and determining whether a pulmonary function of the respective lung lobe is normal or abnormal based on the descriptors.

According to another embodiment, the present disclosure provides a device for detecting pulmonary function based on low-dose CT chest images. The device includes a processor and a memory coupled with the processor. The processor executes computer-readable instructions stored in the memory to perform operations. The operations include receiving a plurality of low-dose chest images; determining, by the processor, a plurality of regions of interest (ROIs) within each low-dose chest image through an image processing model; determining, by the processor, $T_{ij}$ descriptors for the j-th ROI of the i-th chest image through the image processing model of the image processing device; and determining, by the processor, whether the pulmonary function of the respective lung lobe is normal or abnormal based on the descriptors. The plurality of chest image is generated by a low-dose CT method. The plurality of ROIs correspond to five lung lobes. Each descriptor is associated with a radiodensity value of one or more pixels

BRIEF DESCRIPTION OF THE DRAWINGS

In order to describe the manner in which advantages and features of the present disclosure can be obtained, a description of the present disclosure is rendered by reference to specific embodiments thereof, which are illustrated in the appended drawings. These drawings depict only example embodiments of the present disclosure and are therefore not to be considered as limiting its scope.

DETAILED DESCRIPTION

Figure 1:
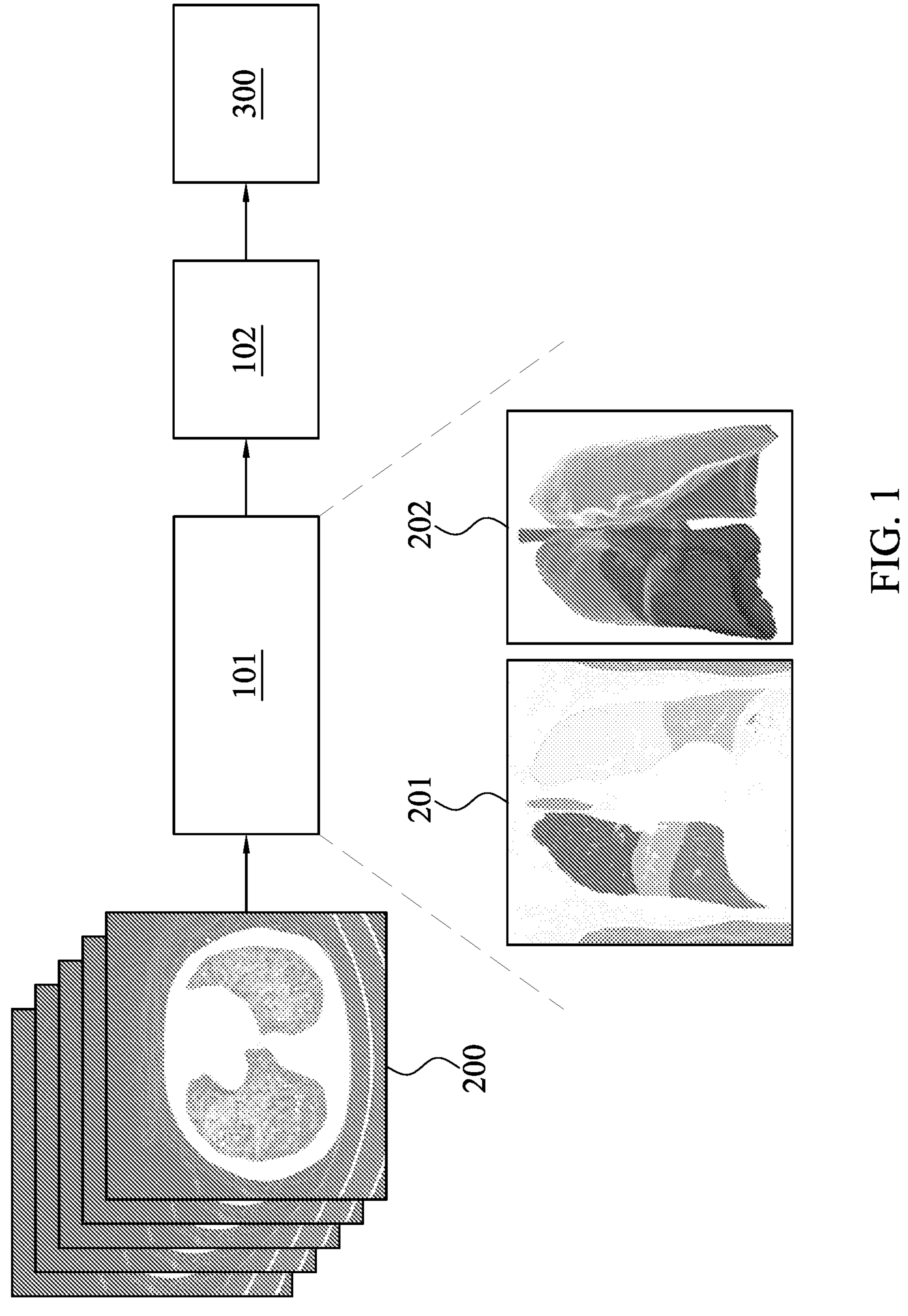
FIG. 1 is a diagram of an architecture for detecting pulmonary function based on low-dose CT images, in accordance with some embodiments of the present disclosure.

The following disclosure provides many different embodiments, or examples, for implementing different features of the provided subject matter. Specific examples of operations, components, and arrangements are described below to simplify the present disclosure. These are, of course, merely examples and are not intended to be limiting. For example, a first operation performed before or after a second operation in the description may include embodiments in which the first and second operations are performed together, and may also include embodiments in which additional operations may be performed between the first and second operations. For example, the formation of a first feature over, on or in a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Time relative terms, such as "prior to," "before," "posterior to," "after" and the like, may be used herein for ease of description to describe the relationship of one operation or feature to another operation(s) or feature(s) as illustrated in the figures. The time relative terms are intended to encompass different sequences of the operations depicted in the figures. Further, spatially relative terms, such as "beneath," "below," "lower," "above," "upper" and the like, may be used herein for ease of description to describe the relationship of one element or feature to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. Relative terms for connections, such as "connect," "connected," "connection," "couple," "coupled," "in communication," and the like, may be used herein for ease of description to describe an operational connection, coupling, or linking between two elements or features. The relative terms for connections are intended to encompass different connections, coupling, or linking of the devices or components. The devices or components may be directly or indirectly connected, coupled, or linked to one another through, for example, another set of components. The devices or components may be wired and/or wirelessly connected, coupled, or linked with each other.

As used herein, the singular terms "a," "an," and "the" may include plural referents unless the context clearly indicates otherwise. For example, reference to a device may include multiple devices unless the context clearly indicates otherwise. The terms "comprising" and "including" may indicate the existences of the described features, integers, steps, operations, elements, and/or components, but may not exclude the existences of combinations of one or more of the features, integers, steps, operations, elements, and/or components. The term "and/or" may include any or all combinations of one or more listed items.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

The nature and use of the embodiments are discussed in detail as follows. It should be appreciated, however, that the present disclosure provides many applicable inventive concepts that can be embodied in a wide variety of specific contexts. The specific embodiments discussed are merely illustrative of specific ways to embody and use the disclosure, without limiting the scope thereof.

FIG. 1 is a diagram of an architecture 10 for detecting pulmonary function based on low-dose computed tomography (CT) images in accordance with some embodiments of the present disclosure. The architecture 10 includes input images 200, output 300, an image processing model 101, and a classifier model 102. In the architecture 10, the image processing model 101 may receive a plurality of chest images 200. The chest images 200 may be obtained by a low-dose CT method. In some embodiments, the radiation unit of a low-dose CT imagining method ranges from approximately 0.3 mSv to approximately 3.0 mSv. A low-dose CT examination would be less physically harmful for a human. However, the CT chest images 200 include low resolution and high noise.

In some embodiments, the CT chest images 200 may be chest CT images of a human. The CT chest images 200 may include one or more organs of a human. For example, the CT chest images 200 may include the lungs or heart, or bones, such as thoracic vertebrae, ribs, sternum, and/or clavicle. In some embodiments, the CT chest images 200 may include a two-dimensional (2D) image or a three-dimensional (3D) image.

The CT chest images 200 are inputted to or applied to the image processing model 101. The image processing model 101 may include, but is not limited to, object detection, semantic segmentation, and localization models. The image processing model may include U-Net, FCN (fully convolutional network), DeconvNet (deconvolution network), SegNet (segmentation network), DeepLab, RefineNet, PSPNet (pyramid scene parsing network), or GSCNN (gated shape convolution neural network). The image processing model can be a deep learning model. The U-Net can be a convolutional neural network for biomedical image segmentation. The neural network is based on the fully convolutional network and its architecture was modified and extended to work with fewer training images and to yield more precise segmentations.

The image processing model 101 may analyze one or more pixels in the CT chest images 200. The image processing model 101 receives the CT chest images 200 and detects each pixel in each CT chest image 200. The image processing model 101 may analyze different organs in each CT chest image 200. Through applying the CT chest images 200 to the image processing model 101, a plurality of regions of interest (ROIs) within each CT chest image 200 can be determined. Thus, the noises related to protein and adipose can be removed or smoothed. In some embodiments, the plurality of ROIs correspond to five lung lobes.

The image processing model 101 is configured to extract or determine $T_{ij}$ descriptors for the j-th ROI of the i-th chest image 200, wherein i is a positive integer indicative of the number of chest images 200, and j is a positive integer indicative of the number of ROIs. Each of the descriptors is associated with the radiodensity values of one or more pixels in one chest image 200. The radiodensity values are represented in Hounsfield units (HU). In some embodiments, the $T_{ij}$ descriptors may be generated or determined based on the radiodensity values of one or more pixels of the j-th ROIs of the i-th chest image 200. In some embodiments, the each descriptor is further associated with at least one of: a serial number of ROI, a serial number of chest image, or coordinate values of one or more pixels. In some embodiments, the descriptors for the chest images 200 are determined based on one of: the scale-invariant feature transform (SIFT) algorithm, the dense trajectory (DT) algorithm, or the improved dense trajectory (iDT) algorithm. The descriptors may be scalars or vectors.

The image processing model 101 outputs the descriptors of the chest images 200 and/or the chest images 200. The descriptors of the chest images 200 and/or the chest images 200 can be applied to the classifier model 102.

The classifier model 102 may include at least one of a support vector machine, a decision tree model, a neutral network, a random forest, or a regression model. The regression model may include a linear regression model exclusive to the lung lobes.

The classifier model 102 is configured to determine whether a pulmonary function associated with the chest images 200 is normal or abnormal based on the corresponding descriptors.

In some embodiments, the classifier model 102 analyzes the descriptors and determines the pulmonary function based on the analysis results of the descriptors. In general, if the radiodensity values are high, it is determined that the corresponding image is relatively opaque; and if the radiodensity values are small, it is determined that the corresponding image is relatively transparent. The radiodensity value of air is −1000 HU. If a lung lobe includes sufficient air, the pulmonary function of the lung lobe is normal. If the lung lobe does not include sufficient air, the pulmonary function of the long lobe is abnormal. That is, if it is determined that the descriptor of one or more pixels is greater than a threshold (the threshold may be ranged from −900 to −1024 HU), the pulmonary function of the one or more pixels is normal. If it is determined that the descriptor of one or more pixels is smaller than the threshold (the threshold may be ranged from −900 to −1024 HU), the pulmonary function of the one or more pixels is abnormal. Since the descriptor of one or more pixels, instead of the rasiodensity value of each pixel, are applied to classifier model 102, the noises due the low-dose CT method may be smoothed. The classifier model 102 may be configured to classify pixels of all lung lobes and determine whether the pulmonary function of the lung lobes is normal or not.

The classifier model 102 may calculate an average of the corresponding descriptors. In this way, the dimensionality of the descriptors can be reduced. The classifier model 102 is configured to determine that the pulmonary function of the respective lung lobe is normal in response to the average of the corresponding descriptors being greater than the threshold. The classifier model 102 is configured to determine that the pulmonary function of the respective lung lobe is abnormal in response to the average of the corresponding descriptors being smaller than the threshold. In some embodiments, the classifier model 102 may determine whether the pulmonary function is normal or abnormal based on the feature vector.

The classifier model 102 may be configured to determine whether a value of FEV1/FVC is greater or less than 70%. FEV1 indicates "forced expiratory volume in one second," and FVC indicates "forced vital capacity."

In another embodiment, through the image processing model 101, the CT chest images 200 may be transformed into a three-dimensional (3D) chest image 201. Through the image processing model 101, the one or more corresponding pixels in different CT chest images 200 may be transformed into one or more voxels of the chest image 201. Through the image processing model 101, semantic segmentation may be conducted for the plurality of ROIs of the chest image 201. Thus, the noises related to protein and adipose can be removed or smoothed. The 3D chest image 202 may be generated after the semantic segmentation. Upon semantic segmentation, the chest image 202 clearly shows voxels of five lung lobes. The image processing model 101 is configured to extract or determine $T_j$ descriptors for the j-th ROI of the 3D chest image 202, wherein j is a positive integer indicative of the number of ROIs. Each of the descriptors is associated with the radiodensity values of one or more voxels in one chest image 202. The radiodensity values are represented in Hounsfield units (HU). In some embodiments, the $T_j$ descriptors may be generated or determined based on the radiodensity values of one or more voxels of the j-th ROIs of the 3D chest image 202. In some embodiments, the each descriptor is further associated with at least one of: a serial number of ROI, or coordinate values of one or more voxels. In some embodiments, the descriptors for the chest image 202 are determined based on one of: the scale-invariant feature transform (SIFT) algorithm, the dense trajectory (DT) algorithm, or the improved dense trajectory (iDT) algorithm. The descriptors may be scalars or vectors.

The image processing model 101 outputs the descriptors of the chest image 202 and/or the chest image 202. The descriptors of the chest image 202 and/or the chest image 202 can be applied to the classifier model 102.

The classifier model 102 may include at least one of a support vector machine, a decision tree model, a neutral network, a random forest, or a regression model. The regression model may include a linear regression model exclusive to the lung lobes.

The classifier model 102 is configured to determine whether a pulmonary function associated with the input chest images 200 is normal or abnormal based on the corresponding descriptors.

In some embodiments, the classifier model 102 analyzes the descriptors and determines the pulmonary function based on the analysis results of the descriptors. In general, if the radiodensity values are high, it is determined that the corresponding image is relatively opaque; and if the radiodensity values are small, it is determined that the corresponding image is relatively transparent. The radiodensity value of air is −1000 HU. If a lung lobe includes sufficient air, the pulmonary function of the lung lobe is normal. If the lung lobe does not include sufficient air, the pulmonary function of the long lobe is abnormal. That is, if it is determined that the descriptor of one or more voxels is greater than a threshold selected between −900 to −1024 HU, the pulmonary function of the one or more voxels is normal. If it is determined that the descriptor of one or more voxels is smaller than the threshold selected between −900 to −1024 HU, the pulmonary function of the one or more voxels is abnormal. Since the descriptor of one or more voxels, instead of the rasiodensity value of each voxel, are applied to classifier model 102, the noises due the low-dose CT method may be smoothed. The classifier model 102 may be configured to classify voxels of all lung lobes and determine whether the pulmonary function of the lung lobes is normal or not.

The classifier model 102 may calculate an average of the corresponding descriptors. In this way, the dimensionality of the descriptors can be reduced. The classifier model 102 is configured to determine that the pulmonary function of the respective lung lobe is normal in response to the average of the corresponding descriptors being greater than a threshold. The classifier model 102 is configured to determine that the pulmonary function of the respective lung lobe is abnormal in response to the average of the corresponding descriptors being smaller than the threshold. In some embodiments, the classifier model 102 may determine whether the pulmonary function is normal or abnormal based on the feature vector.

The classifier model 102 may be configured to determine whether a value of FEV1/FVC is greater or less than 70%. FEV1 indicates "forced expiratory volume in one second," and FVC indicates "forced vital capacity."

In a further embodiment, the image processing model 101 may analyze one or more pixels in the CT chest images 200. The image processing model 101 receives the CT chest images 200 and detects each pixel in each CT chest image 200. The image processing model 101 may analyze different organs in each CT chest image 200. Through applying the CT chest images 200 to the image processing model 101, a plurality of ROIs within each CT chest image 200 can be determined. Thus, the noises related to protein and adipose can be removed or smoothed. In some embodiments, the plurality of ROIs correspond to five lung lobes.

Through the image processing model 101, the CT chest images 200 may be transformed into a three-dimensional (3D) chest image 201 or 202. Through the image processing model 101, the one or more corresponding pixels in different CT chest images 200 may be transformed into one or more voxels of the chest image 201. Since the semantic segmentation have been be conducted for the plurality of ROIs of the chest images 200, after the plurality of ROIs can be obtained in the chest image 201 or 202. The 3D chest image 202 may show the ROIs more clearly. The chest image 202 clearly shows voxels of five lung lobes.

The image processing model 101 is configured to extract or determine $T_j$ descriptors for the j-th ROI of the 3D chest image 202, wherein j is a positive integer indicative of the number of ROIs. Each of the descriptors is associated with the radiodensity values of one or more voxels in one chest image 202. The radiodensity values are represented in Hounsfield units (HU). In some embodiments, the $T_j$ descriptors may be generated or determined based on the radiodensity values of one or more voxels of the j-th ROIs of the 3D chest image 202. In some embodiments, the each descriptor is further associated with at least one of: a serial number of ROI, or coordinate values of one or more voxels. In some embodiments, the descriptors for the chest image 202 are determined based on one of: the scale-invariant feature transform (SIFT) algorithm, the dense trajectory (DT) algorithm, or the improved dense trajectory (iDT) algorithm. The descriptors may be scalars or vectors.

The image processing model 101 outputs the descriptors of the chest image 202 and/or the chest image 202. The descriptors of the chest image 202 and/or the chest image 202 can be applied to the classifier model 102.

The classifier model 102 is configured to determine whether a pulmonary function associated with the input chest images 200 is normal or abnormal based on the corresponding descriptors.

In some embodiments, the classifier model 102 analyzes s the descriptors and determines the pulmonary function based on the analysis results of the descriptors. In general, if the radiodensity values are high, it is determined that the corresponding image is relatively opaque; and if the radiodensity values are small, it is determined that the corresponding image is relatively transparent. The radiodensity value of air is −1000 HU. If a lung lobe includes sufficient air, the pulmonary function of the lung lobe is normal. If the lung lobe does not include sufficient air, the pulmonary function of the long lobe is abnormal. That is, if it is determined that the descriptor of one or more voxels is greater than a threshold selected between −900 to −1024 HU, the pulmonary function of the one or more voxels is normal. If it is determined that the descriptor of one or more voxels is smaller than the threshold selected between −900 to −1024 HU, the pulmonary function of the one or more voxels is abnormal. Since the descriptor of one or more voxels, instead of the rasiodensity value of each voxel, are applied to classifier model 102, the noises due the low-dose CT method may be smoothed. The classifier model 102 may be configured to classify voxels of all lung lobes and determine whether the pulmonary function of the lung lobes is normal or not.

The classifier model 102 may calculate an average of the corresponding descriptors. In this way, the dimensionality of the descriptors can be reduced. The classifier model 102 is configured to determine that the pulmonary function of the respective lung lobe is normal in response to the average of the corresponding descriptors being greater than a threshold. The classifier model 102 is configured to determine that the pulmonary function of the respective lung lobe is abnormal in response to the average of the corresponding descriptors being smaller than the threshold. In some embodiments, the classifier model 102 may determine whether the pulmonary function is normal or abnormal based on the feature vector.

The classifier model 102 may be configured to determine whether a value of FEV1/FVC is greater or less than 70%. FEV1 indicates "forced expiratory volume in one second," and FVC indicates "forced vital capacity."

Figure 2:
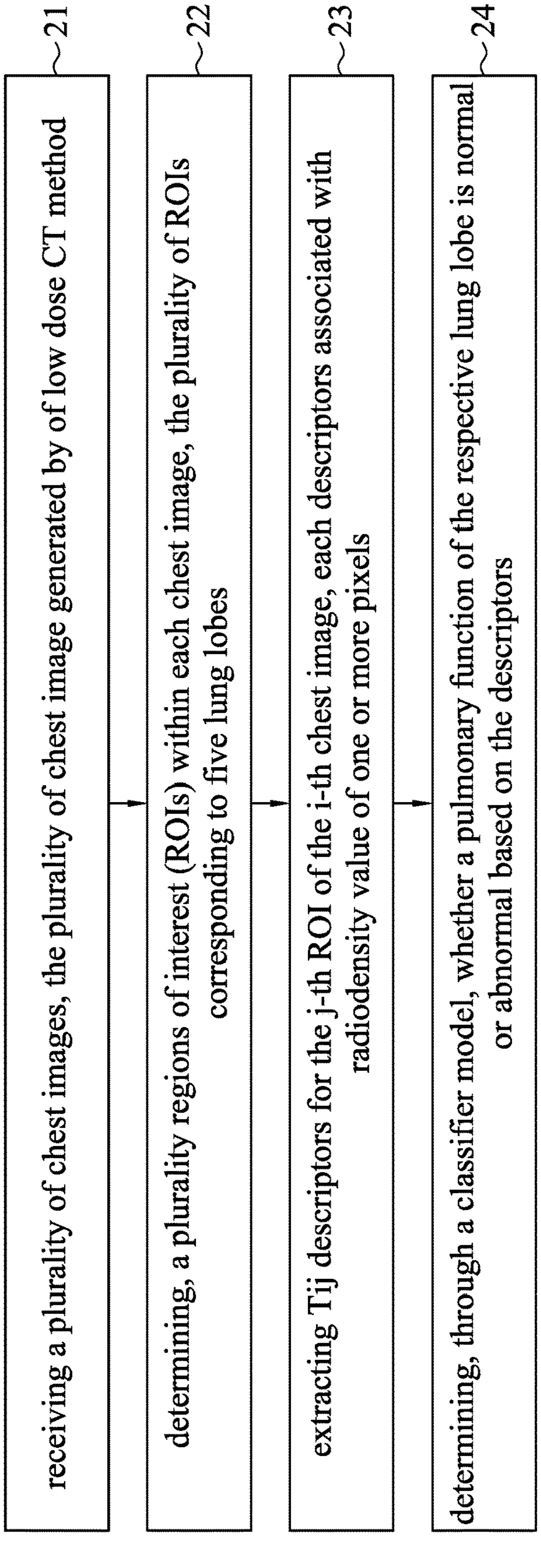
FIG. 2 is a flowchart showing a method of detecting pulmonary function based on low-dose CT images, in accordance with some embodiments.

FIG. 2 is a flowchart showing a method 20 of detecting pulmonary function based on low-dose CT images of the lungs, in accordance with some embodiments. The method 20 includes operations 21, 22, 23, and 24 related to an architecture 10 of FIG. 1. In some embodiments, this method 20 may be performed by one or more models. The models may be artificial intelligence (AI) models. In some embodiments, a memory can store instructions, which may be executed by a processor to perform the method 20. The models may be similar or identical to those described in the architecture 10 of FIG. 1. The memory and the processor may be similar or identical to those described in the computer device 900 shown in FIG. 5.

In operation 21, a plurality of chest images 200 (as shown in FIG. 1) generated by a low-dose CT method are received by the architecture 10. The plurality of chest images 200 may be 2D images. The plurality of chest images 200 include one or more organs. For example, the plurality of chest images may include the lungs, heart, thoracic vertebrae, ribs, sternum, clavicle, or others.

In operation 22, a plurality of regions of interest (ROIs) in the plurality of chest images 200 are determined through applying the plurality of chest images to the image processing model 101 (e.g., the U-Net model). The U-Net model is a deep learning model. In some embodiments, the determination may include detecting or determining a plurality of regions of interest (ROIs) within each chest image. The plurality of ROIs are associated with an organ, such as the lungs or the lobes of the lung. In some embodiments, the determination may include determining a boundary of the lungs based on a semantic segmentation so as to determine the location of the lungs.

In operation 23, $T_{ij}$ descriptors for the j-th ROI of the i-th chest image 200 are extracted or determined. The extraction or determination of the descriptors may be carried out through the image processing model 101. Each of the descriptors is associated with the radiodensity value of one or more pixels. In the embodiment, the descriptors may be scalars or vectors. In some embodiments, the each descriptor is further associated with at least one of: a serial number of ROI, a serial number of chest image, or coordinate values of one or more pixels. In some embodiments, the descriptors for the chest images 200 are determined based on one of: the scale-invariant feature transform (SIFT) algorithm, the dense trajectory (DT) algorithm, or the improved dense trajectory (iDT) algorithm.

In some embodiments, the chest images 200 may be transformed into a 3D chest image (e.g., through the image processing model 101). $T_j$ descriptors for the j-th ROI of the chest image 202 are extracted or determined. The extraction or determination of the descriptors may be carried out through the image processing model 101. Each of the descriptors is associated with the radiodensity value of one or more voxels of the chest image 202. In the embodiment, the descriptors may be scalars or vectors. In some embodiments, the each descriptor is further associated with at least one of: a serial number of ROI, or coordinate values of one or more voxels. In some embodiments, the descriptors for the chest image 202 are determined based on one of: the scale-invariant feature transform (SIFT) algorithm, the dense trajectory (DT) algorithm, or the improved dense trajectory (iDT) algorithm.

In operation 24, a pulmonary function of the respective lung lobe is determined by the classifier model 102 of the architecture 10. The classifier model 102 may include at least one of a support vector machine, a decision tree model, a neutral network, a random forest, or a regression model. The regression model may include a linear regression model exclusive to the lung lobes. The classifier model 102 determines whether the pulmonary function of the respective lung lobe is normal or abnormal based on the descriptors.

In some embodiments, the pulmonary function of the respective lung lobe is determined as normal in response to an average of the corresponding descriptors being greater than a threshold; the pulmonary function of the respective lung lobe is determined as abnormal in response to the average of the corresponding descriptors being smaller than the threshold.

The descriptors can be applied to the classifier model 102 to determine whether a pulmonary function of the respective lung lobe is normal or abnormal based on the descriptors. Since the descriptor of one or more pixels (or voxels), instead of the rasiodensity value of each pixel (or each voxel), are applied to classifier model 102, the noises due the low-dose CT method may be smoothed.

Once whether the pulmonary function of the respective lung lobe is determined, the classifier model 102 can determine whether pulmonary function associated with the input chest images 200 is normal or abnormal (e.g., by a majority rule). The classifier model 102 may be configured to determine whether a value of FEV1/FVC associated with the input chest images 200 is greater or less than 70%.

Figure 3:
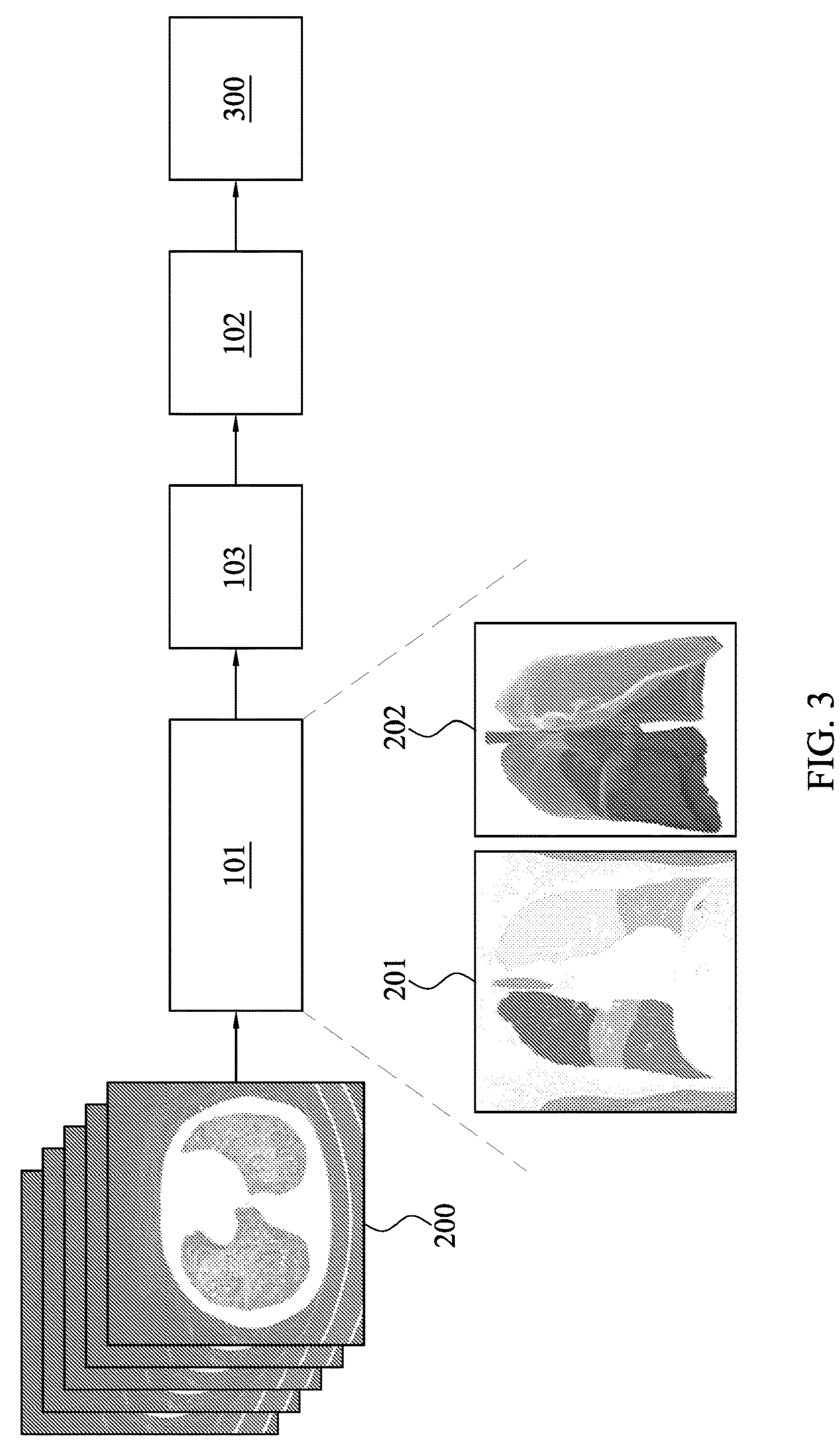
FIG. 3 is a diagram of an architecture for detecting pulmonary function based on low-dose CT images, in accordance with some embodiments of the present disclosure.

FIG. 3 is a diagram of an architecture 10' for detecting pulmonary function based on low-dose computed tomography (CT) images of the lungs in accordance with some embodiments of the present disclosure. The architecture 10' is similar to the architecture 10 of FIG. 1, except that the architecture 10' further includes an encoder 103. The architecture 10' may be used for providing a higher accuracy of the CT chest images 200.

In some embodiments, the signals of the chest image 202 may include high noises. To filter or smooth the noises (e.g., due to the low-dose CT method) efficiently, the output data of the image processing model 101 (e.g., the chest images 200 and the corresponding descriptors after semantic segmentation or the chest image 202 and the corresponding descriptors after semantic segmentation) is applied to the encoder 103.

The encoder 103 may encode the descriptors of the chest images 200 (or the descriptors of the chest image 202) to feature vectors. After the encoder 103, the dimensionality of the descriptors may be reduced. In an embodiment, that the $T_{ij}$ descriptors of the j-th ROIs of the i-th chest image 200 (which may be scalars or vectors) would be encoded as one feature vector. In another embodiment, that the $T_j$ descriptors of the j-th ROIs of the chest image 202 (which may be scalars or vectors) would be encoded as one feature vector. The feature vectors for the chest images 200 (or for the chest image 202) can be generated or determined by the encoder 103. The feature vectors then are applied to the classifier model 102.

In some embodiments, the encoder 103 may extract a feature vector for the j-th ROI of the i-th chest image 200 based on the $T_{ij}$ descriptors. The encoder 103 may transform the $T_{ij}$ descriptors to a feature vector for the j-th ROI of the i-th chest image 200. In some embodiments, the transformation may be related to a matrix transformation. A feature vector for the j-th ROI of the i-th chest image 200 may be encoded through applying the $T_{ij}$ descriptors to a k-mean algorithm. A feature vector for the j-th ROI of the i-th chest image 200 may be encoded through averaging the values of each dimension of the $T_{ij}$ descriptors.

In some embodiments, the encoder 103 may extract a feature vector for the j-th ROI of the chest image 202 based on the $T_j$ descriptors. The encoder 103 may transform the $T_j$ descriptors to a feature vector for the j-th ROI of the chest image 202. In some embodiments, the transformation may be related to a matrix transformation. A feature vector for the j-th ROI of the chest image 202 may be encoded through applying the $T_j$ descriptors to a k-mean algorithm. A feature vector for the j-th ROI of the chest image 202 may be encoded through averaging the values of each dimension of the $T_j$ descriptors.

The classifier model 102 may determine whether a value of FEV1/FVC is greater or less than 70% based on the descriptors.

Figure 4:
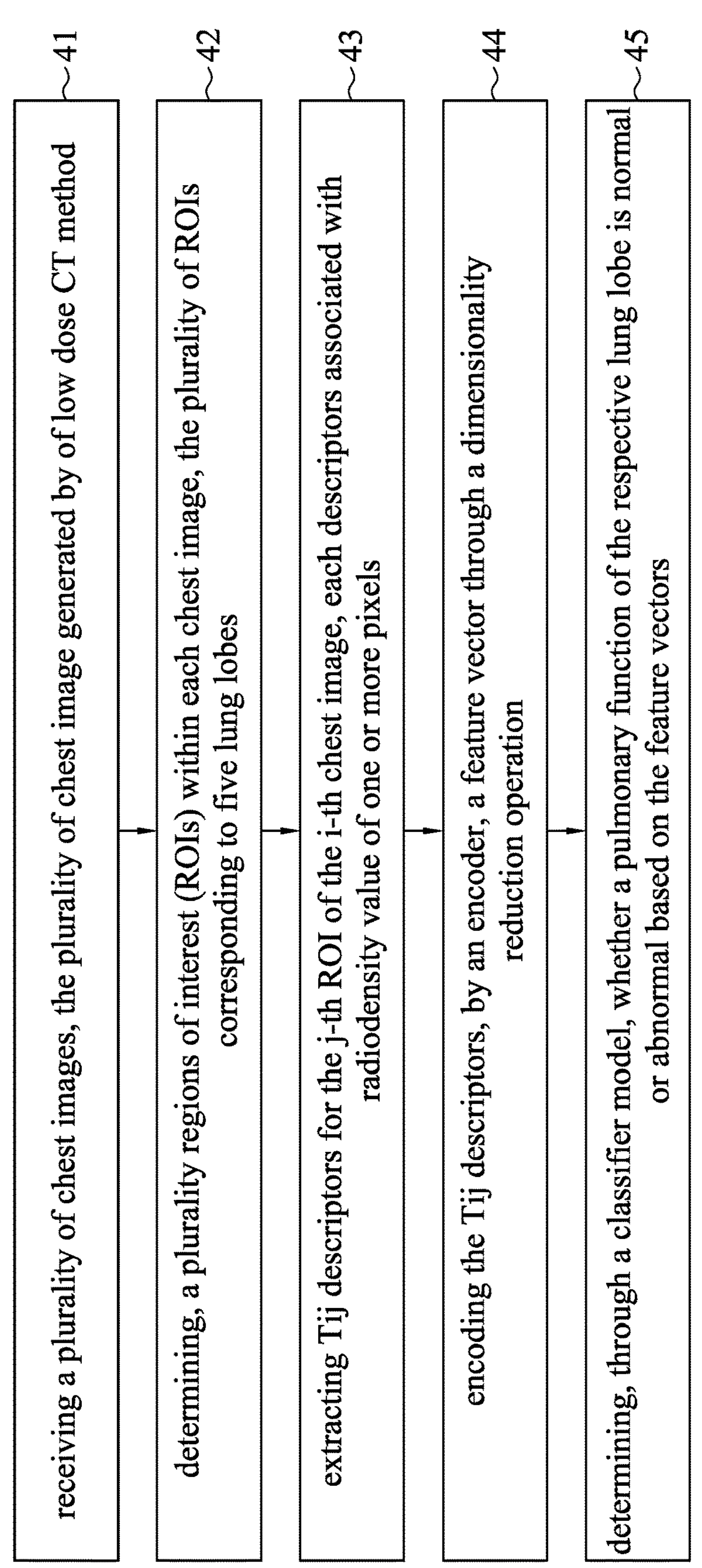
FIG. 4 is a flowchart showing a method of detecting pulmonary function based on low-dose CT images of the lungs, in accordance with some embodiments.

FIG. 4 is a flowchart showing a method 40 of detecting pulmonary function based on low-dose CT images of the lungs, in accordance with some embodiments. The method 40 includes operations 41, 42, 43, 44, and 45. The method 40 may be related to an architecture 10' of FIG. 3. In some embodiments, this method 40 may be performed by one or more models. The models may be artificial intelligence (AI) models. In some embodiments, a memory can store instructions, which may be executed by a processor to perform the method 40. The models may be similar or identical to those described in the architecture 10' of FIG. 3. The memory and the processor may be may be similar or identical to those described in the computer device 900 shown in FIG. 5.

In operation 41, a plurality of chest images 200 (as shown in FIG. 3) generated by a low-dose CT method are received by the architecture 10'. The plurality of chest images 200 may be 2D images. The plurality of chest images 200 include one or more organs. For example, the plurality of chest images may include the lungs, heart, thoracic vertebrae, ribs, sternum, clavicle, or others.

In operation 42, a plurality of regions of interest (ROIs) in the plurality of chest images 200 are determined through applying the plurality of chest images to the image processing model 101 of the architecture 10'. The U-Net model is a deep learning model. In some embodiments, the determination may include detecting or determining a plurality of regions of interest (ROIs) within each chest image. The plurality of ROIs are associated with organs such as the lungs. In some embodiments, the determination may include determining a boundary of the lungs based on a semantic segmentation so as to determine the location of the lungs.

In operation 43, $T_{ij}$ descriptors for the j-th ROI of the i-th chest image 200 are extracted or determined. The extraction or determination of the descriptors may be carried out through the image processing model 101. Each of the descriptors is associated with the radiodensity value of one or more pixels. In some embodiments, the each descriptor is further associated with at least one of: a serial number of ROI, a serial number of chest image, or coordinate values of one or more pixels. In some embodiments, the descriptors for the chest images 200 are determined based on one of: the scale-invariant feature transform (SIFT) algorithm, the dense trajectory (DT) algorithm, or the improved dense trajectory (iDT) algorithm. In the embodiment, the descriptors may be scalars or vectors.

In some embodiments, the chest images 200 may be transformed into a 3D chest image (e.g., through the image processing model 101). $T_j$ descriptors for the j-th ROI of the chest image 202 are extracted or determined. The extraction or determination of the descriptors may be carried out through the image processing model 101. Each of the descriptors is associated with the radiodensity value of one or more voxels of the chest image 202. In some embodiments, the each descriptor is further associated with at least one of: a serial number of ROI, a serial number of chest image, or coordinate values of one or more voxels. In some embodiments, the descriptors for the chest image 202 are determined based on one of: the scale-invariant feature transform (SIFT) algorithm, the dense trajectory (DT) algorithm, or the improved dense trajectory (iDT) algorithm. In the embodiment, the descriptors may be scalars or vectors.

In operation 44, the $T_{ij}$ descriptors for the j-th ROI of the i-th chest image 200 are transformed or encoded to a feature vector by the encoder 103 of the architecture 10'. A feature vector for the j-th ROI of the i-th chest image 200 may be encoded or determined through applying the $T_{ij}$ descriptors to a k-mean algorithm. A feature vector for the j-th ROI of the i-th chest image 200 may be encoded or determined through averaging the values of each dimension of the $T_{ij}$ descriptors.

In operation 44, the $T_j$ descriptors for the j-th ROI of the chest image 202 are transformed or encoded to a feature vector by the encoder 103 of the architecture 10'. A feature vector for the j-th ROI of the chest image 202 may be encoded or determined through applying the $T_j$ descriptors to a k-mean algorithm. A feature vector for the j-th ROI of the chest image 202 may be encoded or determined through averaging the values of each dimension of the $T_j$ descriptors.

Encoding the descriptors into a feature vector can efficiently reduce the dimensionality and efficiently filter or smooth the noises of the plurality of chest images 200.

In operation 45, a pulmonary function of the respective lung lobe is determined by the classifier model 102 of the architecture 10'. The classifier model 102 may include at least one of a support vector machine, a decision tree model, a neutral network, a random forest, or a regression model. The regression model may include a linear regression model exclusive to the lung lobes. The classifier model 102 determines whether the pulmonary function of the respective lung lobe is normal or abnormal based on the descriptors.

In some embodiments, the pulmonary function of the respective lung lobe is determined as normal in response to an average of the corresponding descriptors being greater than a threshold; the pulmonary function of the respective lung lobe is determined as abnormal in response to the average of the corresponding descriptors being smaller than the threshold.

The descriptors can be applied to the classifier model 102 to determine whether a pulmonary function of the respective lung lobe is normal or abnormal based on the descriptors. Since the descriptor of one or more pixels (or voxels), instead of the rasiodensity value of each pixel (or each voxel), are applied to classifier model 102, the noises due the low-dose CT method may be smoothed.

Once whether the pulmonary function of the respective lung lobe is determined, the classifier model 102 can determine whether pulmonary function associated with the input chest images 200 is normal or abnormal (e.g., by a majority rule). The classifier model 102 may be configured to determine whether a value of FEV1/FVC associated with the input chest images 200 is greater or less than 70%.

Figure 5:
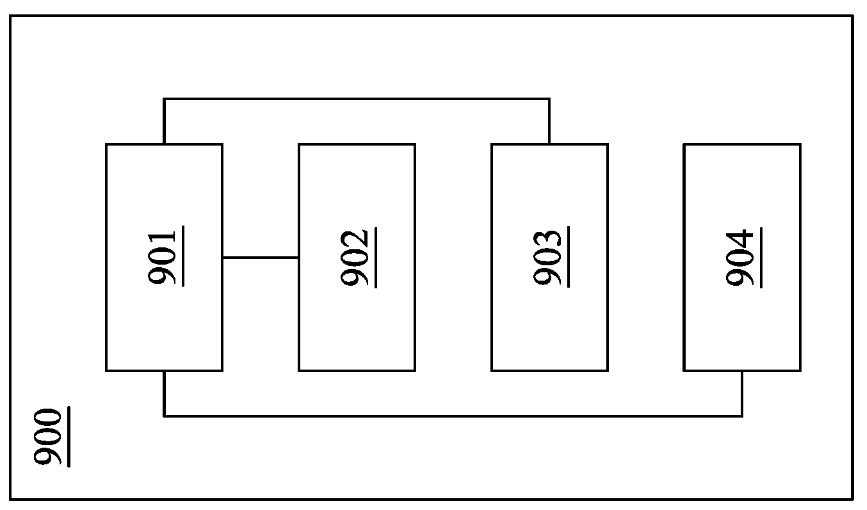
FIG. 5 is a schematic diagram of a computer device according to some embodiments of the present disclosure.

FIG. 5 is a schematic diagram showing a computer device 900 according to some embodiments of the present disclosure. The computer device 900 may be capable of performing one or more procedures, operations, or methods of the present disclosure. The computer device 900 may be a server computer, a client computer, a personal computer (PC), a tablet PC, a set-top box (STB), a personal digital assistant (PDA), a cellular telephone, or a smartphone. The computing device 900 comprises a processor 901, input/output interface 902, a communication interface 903, and a memory 904. The input/output interface 902 is coupled with the processor 901. The input/output interface 902 allows the user to manipulate the computing device 900 to perform the procedures, operations, steps, or methods of the present disclosure (e.g., the procedures, operations, or methods disclosed in FIGS. 1 to 4). The communication interface 903 is coupled with the processor 901. The communication interface 903 allows the computing device 900 to communicate with data outside the computing device 900, for example, receiving data including images and/or any essential features. A memory 904 may be a non-transitory computer readable storage medium. The memory 904 is coupled with the processor 901. The memory 904 has stored program instructions that can be executed by one or more processors (for example, the processor 901).

For example, upon execution of the program instructions stored on the memory 904, the program instructions cause performance of the one or more procedures, operations, or methods disclosed in the present disclosure. For example, the program instructions may cause the computing device 900 to perform, for example, receiving a plurality of chest images generated by a low-dose CT method; determining, by the processor 901, a plurality of regions of interest (ROIs) within each chest image through applying the plurality of chest images to an image processing model; determining, by the processor 901, $T_{ij}$ descriptors for the j-th ROI of the i-th chest image, each descriptor associated with a radiodensity value of one or more pixels; and; determining, by the processor 901, whether a pulmonary function of the respective lung lobe is normal or abnormal based on the descriptors through a classifier model.

The scope of the present disclosure is not intended to be limited to the particular embodiments of the process, machine, manufacture, and composition of matter, means, methods, steps, and operations described in the specification. As those skilled in the art will readily appreciate from the disclosure of the present disclosure, processes, machines, manufacture, composition of matter, means, methods, steps, or operations presently existing or later to be developed that perform substantially the same function or achieve substantially the same result as the corresponding embodiments described herein may be utilized according to the present disclosure. Accordingly, the appended claims are intended to include within their scope processes, machines, manufacture, and compositions of matter, means, methods, steps, or operations. In addition, each claim constitutes a separate embodiment, and the combination of various claims and embodiments are within the scope of the disclosure.

The methods, processes, or operations according to embodiments of the present disclosure can also be implemented on a programmed processor. However, the controllers, flowcharts, and modules may also be implemented on a general purpose or special purpose computer, a programmed microprocessor or microcontroller and peripheral integrated circuit elements, an integrated circuit, a hardware electronic or logic circuit such as a discrete element circuit, a programmable logic device, or the like. In general, any device on which resides a finite state machine capable of implementing the flowcharts shown in the figures may be used to implement the processor functions of the present disclosure.

An alternative embodiment preferably implements the methods, processes, or operations according to embodiments of the present disclosure on a non-transitory, computer-readable storage medium storing computer programmable instructions. The instructions are preferably executed by computer-executable components preferably integrated with a network security system. The non-transitory, computer-readable storage medium may be stored on any suitable computer readable media such as RAMs, ROMs, flash memory, EEPROMs, optical storage devices (CD or DVD), hard drives, floppy drives, or any suitable device. The computer-executable component is preferably a processor, but the instructions may alternatively or additionally be executed by any suitable dedicated hardware device. For example, an embodiment of the present disclosure provides a non-transitory, computer-readable storage medium having computer programmable instructions stored therein.

While the present disclosure has been described with specific embodiments thereof, it is evident that many alternatives, modifications, and variations may be apparent to those skilled in the art. For example, various components of the embodiments may be interchanged, added, or substituted in the other embodiments. Also, all of the elements of each figure are not necessary for operation of the disclosed embodiments. For example, one of ordinary skill in the art of the disclosed embodiments would be able to make and use the teachings of the present disclosure by simply employing the elements of the independent claims. Accordingly, embodiments of the present disclosure as set forth herein are intended to be illustrative, not limiting. Various changes may be made without departing from the spirit and scope of the present disclosure.

Even though numerous characteristics and advantages of the present disclosure have been set forth in the foregoing description, together with details of the structure and function of the invention, the disclosure is illustrative only. Changes may be made to details, especially in matters of shape, size, and arrangement of parts, within the principles of the invention to the full extent indicated by the broad general meaning of the terms in which the appended claims are expressed.

What is claimed is:

1. A method of determining a pulmonary function based on low-dose computed tomography (CT) chest images, comprising:
- receiving a plurality of chest images, the plurality of chest image generated by a low-dose CT method;
- determining a plurality of regions of interest (ROIs) within each chest image through applying the plurality of chest images to an image processing model, the plurality of ROIs corresponding to five lung lobes;
- determining $T_{ij}$ descriptors for the j-th ROI of the i-th chest image, each descriptor associated with a radiodensity value of one or more pixels; and
- determining, through a classifier model, whether a pulmonary function of the respective lung lobe is normal or abnormal based on the descriptors,
- wherein the radiodensity values are represented in Hounsfield units, and wherein determining a plurality of regions of interest (ROIs) within each chest image further comprises removing protein and adipose from each chest image.

2. The method of claim 1, wherein determining the pulmonary function of the respective lung lobe further comprises:
- determining that the pulmonary function of the respective lung lobe is normal in response to an average of the corresponding descriptors being greater than a threshold; and
- determining that the pulmonary function of the respective lung lobe is abnormal in response to the average of the corresponding descriptors being smaller than the threshold.

3. The method of claim 1, wherein determining the pulmonary function of the respective lung lobe further comprises:
- determining whether the pulmonary function of the respective lung lobe is normal or abnormal through applying the descriptors to the classifier model.

4. The method of claim 3, wherein the classifier model includes at least one of a support vector machine, a decision tree, a neural network, a random forest, or a regression model.

5. The method of claim 3, wherein each descriptor is further associated with at least one of: a serial number of ROI, a serial number of chest image, or coordinate values of the one or more pixels.

6. The method of claim 3, wherein the $T_{ij}$ descriptors for the j-th ROI of the i-th chest image are determined based on one of: the scale-invariant feature transform (SIFT) algorithm, the dense trajectory (DT) algorithm, or the improved dense trajectory (iDT) algorithm.

7. The method of claim 3, further comprising:
- determining a feature vector for the j-th ROI of the i-th chest image based on the $T_{ij}$ descriptors; and
- determining whether the pulmonary function is normal or abnormal through applying the feature vectors to the classifier model.

8. The method of claim 1, further comprising: determining whether a value of FEV1/FVC is greater or less than 70% through applying the descriptors to the classifier model.

9. The method of claim 1, wherein the image processing model includes a U-NET model.

10. A device for detecting pulmonary function based on low-dose computed tomography (CT) chest images, comprising:
- a processor; and
- a memory coupled with the processor,
- wherein the processor executes computer-readable instructions stored in the memory to perform operations, and the operations comprise:
  - receiving a plurality of chest images, the plurality of chest image generated by a low-dose CT method;
  - determining, by the processor, a plurality of regions of interest (ROIs) within each chest image through applying the plurality of chest images to an image processing model, the plurality of ROIs corresponding to five lung lobes;
  - determining, by the processor, $T_{ij}$ descriptors for the j-th ROI of the i-th chest image, each descriptor associated with a radiodensity value of one or more pixels; and
  - determining, by the processor, whether a pulmonary function of the respective lung lobe is normal or abnormal based on the descriptors through a classifier model,
- wherein the radiodensity values are represented in Hounsfield units, and wherein determining a plurality of regions of interest (ROIs) within each chest image further comprises removing protein and adipose from each chest image.

11. The device of claim 10, wherein determining the pulmonary function of the respective lung lobe further comprises:
- determining that the pulmonary function of the respective lung lobe is normal in response to an average of the corresponding descriptors being greater than a threshold; and
- determining that the pulmonary function of the respective lung lobe is abnormal in response to the average of the corresponding descriptors being smaller than the threshold.

12. The device of claim 10, wherein determining the pulmonary function of the respective lung lobe further comprises:

determining whether the pulmonary function of the respective lung lobe is normal or abnormal through applying the descriptors to the classifier model.

13. The device of claim 12, wherein the classifier model includes at least one of a support vector machine, a decision tree, a neural network, a random forest, or a regression model.

14. The device of claim 12, wherein each descriptor is further associated with at least one of: a serial number of ROI, a serial number of chest image, or coordinate values of the one or more pixels.

15. The device of claim 12, wherein the $T_{ij}$ descriptors for the j-th ROI of the i-th chest image are determined based on one of: the scale-invariant feature transform (SIFT) algorithm, the dense trajectory (DT) algorithm, or the improved dense trajectory (iDT) algorithm.

16. The device of claim 12, wherein the operations further comprise:

determining a feature vector for the j-th ROI of the i-th chest image based on the $T_{ij}$ descriptors; and determining whether the pulmonary function is normal or abnormal through applying the feature vectors to the classifier model.

17. The device of claim 10, wherein the classifier model is configured to determine whether a value of FEV1/FVC is greater or less than 70% based on the descriptors.

18. The device of claim 10, wherein the image processing model include a U-NET model.

* * * * *